(12) United States Patent
Flexman

(10) Patent No.: US 9,283,316 B2
(45) Date of Patent: Mar. 15, 2016

(54) PRIMING ANTICOAGULANT ALIGNMENT FOR BLOOD EXTRACTION

(75) Inventor: Greg Flexman, Cary, NC (US)

(73) Assignee: GRIFOLS, S.A., Barcelona (ES)

( * ) Notice: Subject to any disclaimer, the term of this patent is extended or adjusted under 35 U.S.C. 154(b) by 244 days.

(21) Appl. No.: 14/122,726

(22) PCT Filed: May 24, 2012

(86) PCT No.: PCT/ES2012/070374
§ 371 (c)(1),
(2), (4) Date: Nov. 27, 2013

(87) PCT Pub. No.: WO2012/164125
PCT Pub. Date: Dec. 6, 2012

(65) Prior Publication Data
US 2014/0100507 A1    Apr. 10, 2014

Related U.S. Application Data

(60) Provisional application No. 61/490,856, filed on May 27, 2011, provisional application No. 61/493,566, filed on Jun. 6, 2011.

(51) Int. Cl.
*A61M 37/00*  (2006.01)
*A61M 1/36*   (2006.01)
*A61M 1/38*   (2006.01)
*A61M 1/34*   (2006.01)

(52) U.S. Cl.
CPC ........... *A61M 1/3672* (2013.01); *A61M 1/3643* (2013.01); *A61M 1/3644* (2014.02); *A61M 1/38* (2013.01); *A61M 1/3496* (2013.01)

(58) Field of Classification Search
CPC ............ A61M 1/3672; A61M 1/3644; A61M 1/3643; A61M 1/38
See application file for complete search history.

(56) References Cited

U.S. PATENT DOCUMENTS

| 6,743,192 B1 | 6/2004 | Sakota et al. |
| 2005/0209522 A1 | 9/2005 | Tadokaro et al. |
| 2009/0259164 A1 | 10/2009 | Pages et al. |

FOREIGN PATENT DOCUMENTS

WO    WO 94/12223 A1    6/1994

OTHER PUBLICATIONS

International search report dated Sep. 11, 2012 in corresponding PCT Application No. PCT/ES2012/070374 filed May 24, 2012.

*Primary Examiner* — Leslie Deak
(74) *Attorney, Agent, or Firm* — RatnerPrestia

(57) ABSTRACT

Methods and devices are described for reducing anticoagulant dilution of collected blood components during blood collection.

5 Claims, 5 Drawing Sheets

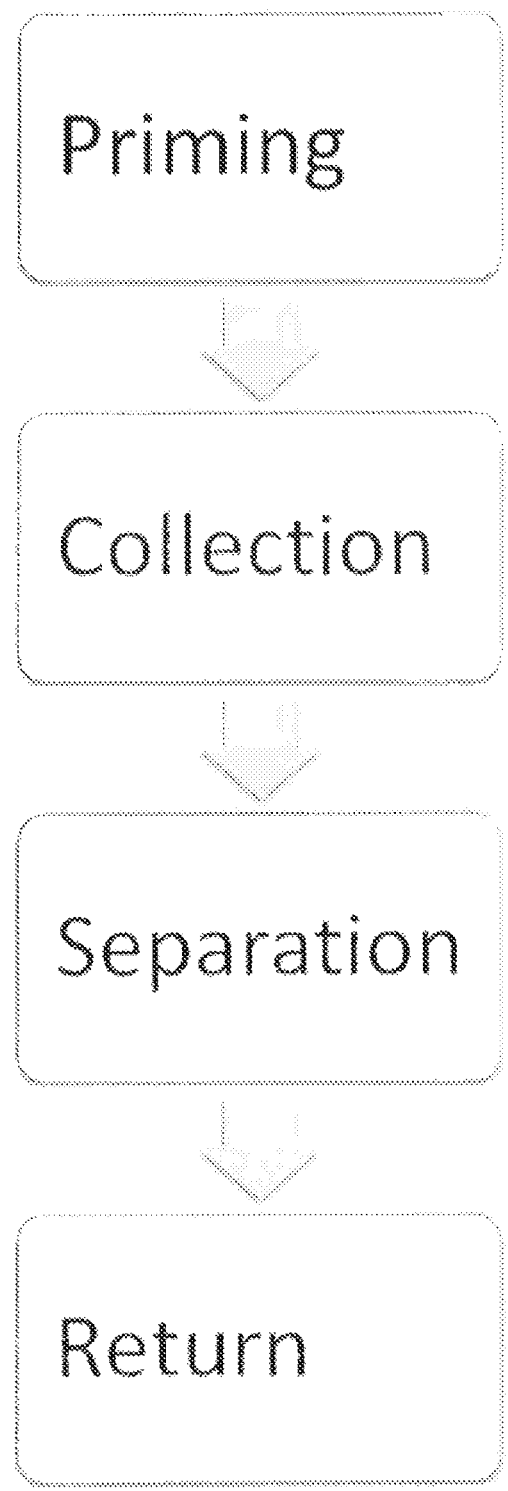

PRIMING ANTICOAGULANT ALIGNMENT FOR BLOOD EXTRACTION

CROSS REFERENCE TO RELATED APPLICATIONS

This application is a 371 application of International Application No. PCT/ES2012/070374, filed May 24, 2012, which claims priority to U.S. Provisional Patent Application No. 61/493,366, filed Jun. 6, 2011 and U.S. Provisional Patent Application No. 61/490,856 filed May 27, 2011, each of which is incorporated by reference in its entirety herein.

TECHNICAL FIELD

Described herein are devices and methods for collecting blood components. More particularly, the methods and devices described herein relate to reducing dilution of collected blood components during blood collection caused by anticoagulant used to prime the collection system prior to the commencement of the collection process; the priming anticoagulant.

BACKGROUND

Apheresis is a procedure in which individual blood components are collected and separated from whole blood that is temporarily withdrawn from a donor. Typically, whole blood is withdrawn through a needle inserted into a vein of a donor's arm; anticoagulant is added to the blood, and it is pumped into a separator such as a centrifugal bowl. Once the whole blood is separated into its various components based on physical characteristics such as density (e.g., red blood cells, white blood cells, platelets, and plasma), one or more of the components can be removed from the centrifugal bowl. The remaining components can be returned to the donor, in some cases with optional compensation fluid to make up for the volume of the removed component or to facilitate transit. The compensation fluid is often saline. The process of drawing whole blood and returning the separated components to the donor continues until the quantity of the desired component has been collected, at which point the process is stopped. A central feature of apheresis systems is that the processed but unwanted components are returned to the donor. Separated blood components may include, for example, a high-density component such as red blood cells, an intermediate-density component such as white blood cells or platelets, or a low-density component such as plasma.

Blood processing systems, such as apheresis systems, typically add an anticoagulant (e.g., sodium citrate/citric acid in saline or dextrose solution) to prevent blood or blood components from clumping and coagulating during collection within the blood collection system or in the collected components. Typically, the anticoagulant is directly mixed with the whole blood as it is drawn from the donor. The ratio of anticoagulant to whole blood may be set to a specific ratio. The U.S. FDA has established particular ratios of anticoagulant to whole blood when collecting source plasma. See, e.g., Kathryn C. Zoon, Director, FDA Center for Biologies Evaluation and Research, Volume Limits for Automated Collection of Source Plasma (Nov. 4, 1992); and see Compliance Policy Guide 0252.110 Volume Limits for Automated Collection of Source Plasma (Mar. 6, 2000) (hereafter collectively referred to as "*FDA Volume limits*"; shown in Table 1, below).

An additional concern is the amount of anticoagulant added to collected components beyond the intended ratio to whole blood. Any additional anticoagulant dilutes the concentration of the collected components in the volume of the fraction (e.g., plasma). This additional volume can complicate or reduce the efficiency of downstream processing of various blood components, particularly plasma. Accordingly, it is desirable to limit any excess in the amount of anticoagulant added to the collected blood components.

A further reason for limiting the amount of anticoagulant added to blood is that the quantity (volume) of the blood component collected from the donor is typically determined by the weight of the collected anticoagulated sample. This weight often includes the anticoagulant used to prime the lines prior to commencing blood collection from the donor. This additional mass contributed by the priming anticoagulant contributes to the apparent mass of the collected blood component. As such, the quantity of the collected blood component is reduced because of the mass of priming anticoagulant. While the difference in mass contributed by the priming anticoagulant in the lines prior to collection may be negligible for a single donation and not of clinical significance to the donor, a consistent mass difference compounds when accumulated over many such donations. Thus, the quantity of blood component(s) that are not collected because of priming anticoagulant becomes significant over numerous collections, such as for commercial-scale preparation of blood components. Described herein are methods for remediating the priming anticoagulant weight contribution by aligning the anticoagulant within the blood collection device so that a reduced volume of pure anticoagulant is directed to the separation system preceding the flow of anticoagulated blood, upon commencing blood collection.

SUMMARY

Described herein is a method of reducing anticoagulant dilution of collected blood components comprising reducing the volume of anticoagulant used during blood component collection, further comprising aligning the anticoagulant within a blood collection device.

Also described herein is a device for reducing the collected volume during blood component collection comprising a means for reducing the volume of anticoagulant used during blood component collection, further comprising a means for aligning the anticoagulant within a blood collection device.

Another aspect described herein relates to a method of reducing collected volume during blood component collection comprising (a) priming and aligning the blood processing equipment with an anticoagulant solution composing: (i) synchronously pumping 2, 11 anticoagulant 1 until anticoagulant is detected by an air/fluid sensor 8 in a withdraw/return line 7 and (1) confirming pump operation and tubing geometry by comparing the number of pump revolutions required to progress the anticoagulant solution between air/fluid sensors 3, 8 to pre-established expectations derived from understanding of pump displacement and tubing length; and (2) confirming proper function of the pumps 2, 11 and cap 6 on the venous access device 5 by holding one pump fixed, and moving the other, while comparing the observed pressure change at a pressure sensor 9, to the expected change given the volume of fluid vs air expected in the lines; and (3) annunciating any discrepancies to operator such that they can take appropriate action, and (ii) synchronously reverse pumping 2, 11 the anticoagulant until the air/anticoagulant interface boundary is present in the priming anticoagulant alignment point 100; (b) proceeding with the collection and separation of blood components comprising connecting a venous-access device 5 to a donor, the venous-access device fluidly connected via the draw/return tubing 7 to a blood separation device; (c) withdrawing whole blood from the donor such that the drawn whole blood is collected in the blood component separation device for processing; (d) separating the withdrawn whole blood into a first blood component and a second blood component using the blood component separation device; (e) extracting at least one blood components from the blood component separation device; (f) returning other components such as erythrocytes, leukocytes, platelets to the donor through a draw/return line.

Another aspect described herein relates to a method of reducing collected volume during blood component collection comprising (a) priming and aligning the blood processing equipment with an anticoagulant solution comprising (i) synchronously pumping 2, 11 anticoagulant 1 until anticoagulant is detected by an air/fluid sensor 3 in a anticoagulant line 4; and (ii) synchronously pumping 2, 11 the anticoagulant until the air/anticoagulant interface boundary is present in the priming anticoagulant alignment point 100; (b) proceeding with the collection and separation of blood components comprising connecting a venous-access device 5 to a donor, the venous-access device fluidly connected via the draw/return tubing 7 to a blood separation device; (c) withdrawing whole blood from the donor such that the drawn whole blood is collected in the blood component separation device for processing; (d) separating the withdrawn whole blood into a first blood component and a second blood component using the blood component separation device; (e) extracting at least one blood components from the blood component separation device; (f) returning other components such as erythrocytes, leukocytes, platelets to the donor through a draw/return line.

Another aspect described herein relates to a device for reducing collected volume during blood component collection comprising: (a) a means for priming and aligning the blood processing equipment with an anticoagulant solution; (b) a means for inserting a venous-access device 5 into a donor, the venous-access device fluidly connected via the draw/return tubing 7 to a blood separation device; (c) a means for withdrawing whole blood from the donor such that the drawn whole blood is collected in the blood component separation device for processing; (d) a means for separating the withdrawn whole blood into a first blood component and a second blood component using the blood component separation device; (e) a means for extracting the second blood component (plasma) from the blood component separation device; (f) a means for returning the first blood component (erythrocytes, leukocytes, platelets) to the donor through a draw/return line.

Another aspect described herein relates to a non-diluting blood-processing device for collecting and exchanging blood components comprising: (a) an anticoagulant reservoir; (b) a venous-access device for drawing whole blood from a donor and returning unused blood components to the donor; (c) an anticoagulant line fluidly connecting the anticoagulant reservoir to the venous-access device; (d) a blood component separation device for separating whole blood drawn from a donor into a first blood component and a second blood component, the blood component separation device configured to send the second blood component to a second blood component storage container; (e) a withdraw/return line fluidly connecting the venous-access device and the blood component separation device for drawing whole blood from a donor and returning the first blood component to the donor; (f) at least one pump fluidly connected to each of the anticoagulant and withdraw/return lines; (g) at least one liquid/air detector fluidly connected to the anticoagulant line; (h) two liquid/air detectors fluidly connected to the withdraw/return line; wherein the first liquid/air detector 200 is connected to the withdraw/return line immediately adjacent to the venous-access device and the second liquid/air detector is connected to the withdraw/return line between the first liquid/air detector and the withdraw/return pump; (i) at least one pressure sensor fluidly connected to the withdraw/return line between the blood component separation device and the venous-access device for determining a pressure within the withdraw/return line; wherein the pump connected to the withdraw/return line controls a flow rate within the withdraw/return line, the pump controlling the flow rate based on the determined pressure.

Another aspect described herein relates to a non-diluting blood-processing device for collecting and exchanging blood components comprising: (a) a means for priming and aligning the blood processing equipment with an anticoagulant solution comprising synchronously pumping anticoagulant until anticoagulant is detected by a first air/fluid sensor in a withdraw/return line; (b) a means for inserting a venous-access device into a donor, the venous-access device fluidly connected via the draw/return tubing to a blood separation device; (c) a means for withdrawing whole blood from the donor such that the drawn whole blood is collected in the blood component separation device for processing; (d) a means for separating the withdrawn whole blood into a first blood component and a second blood component using the blood component separation device; (e) a means for extracting the second blood component (plasma) from the blood component separation device; (f) a means for returning the first blood component (erythrocytes, leukocytes, platelets) to the donor through the draw/return line.

Another aspect described herein relates to a non-diluting blood-processing device for collecting and exchanging blood components comprising a means for reducing the volume of anticoagulant used during blood collection further comprising a means for aligning the anticoagulant within a blood collection device.

Another aspect described herein relates to a method of collecting and exchanging blood components using a non-diluting blood processing device comprising: (a) priming and aligning a non-diluting blood processing device with an anticoagulant solution comprising synchronously pumping anticoagulant until anticoagulant is detected by a first air/fluid sensor in a withdraw/return line; (b) inserting a venous-access device into a donor, the venous-access device fluidly connected via the draw/return tubing to a blood separation device; (c) withdrawing whole blood from the donor such that the drawn whole blood is collected in the blood component separation device for processing; (d) separating the withdrawn whole blood into a first blood component and a second blood component using the blood component separation device; (e) extracting the second blood component (plasma) from the blood component separation device; (f) returning the first blood component (erythrocytes, leukocytes, platelets) to the donor through the draw/return line.

BRIEF DESCRIPTION OF THE DRAWINGS

These aspects and other features described herein are better understood when the following Detailed Description is read with reference to the accompanying figures.

1 Anticoagulant reservoir

2 Anticoagulant pump

Figure 2:
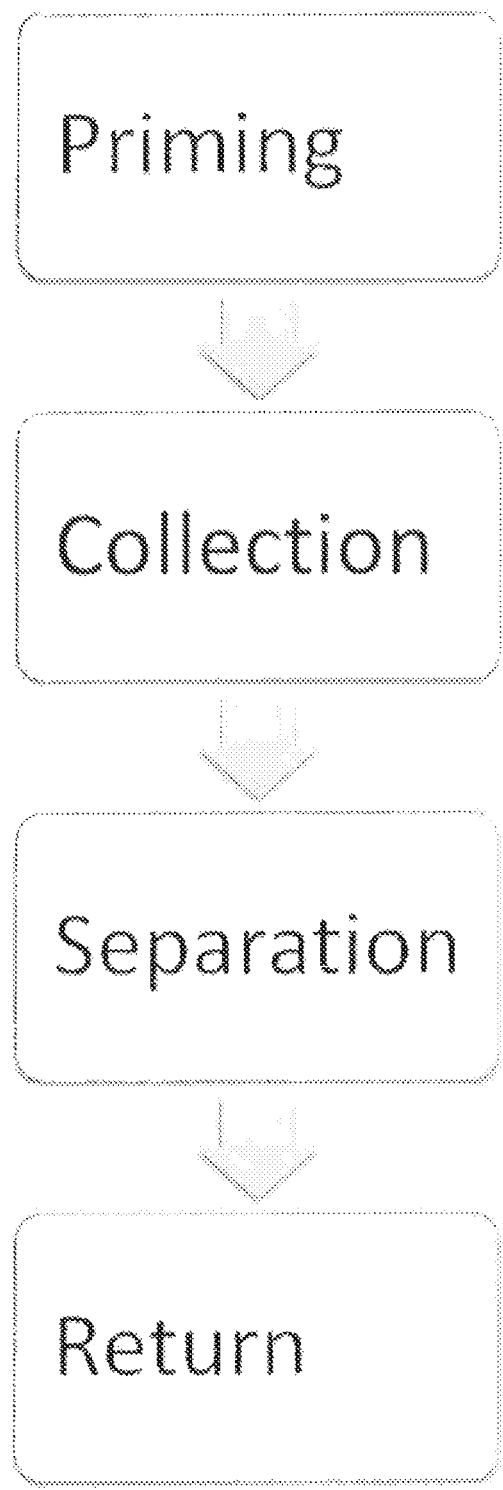

3 Liquid/air detector
4 Anticoagulant tubing to Y-connector and venous access device
5 Y-connector and venous access device
6 Removable cap on venous access device
7 Blood withdraw/return tubing to separation and collection equipment
8 Liquid/air detector
9 Pressure Sensor
10 Filter
11 Pump for anticoagulated blood and returned components
12 Separation, collection, and return components (not individually illustrated)
100 Priming anticoagulant alignment point in the distal withdraw/return space FIG. 2 is a flow chart of typical process steps used by automated blood collection devices. The process involves: Priming (synchronously advance pumps until anticoagulant is detected at withdraw/return liquid/air detector); Collection (insert venous access device into donor's vein; advance pumps drawing whole blood from donor and mixing with anticoagulant); Separation (centrifugally separate blood components based on density; collect and retain desired component); and Return (return unneeded blood components to donor).

Figure 3:
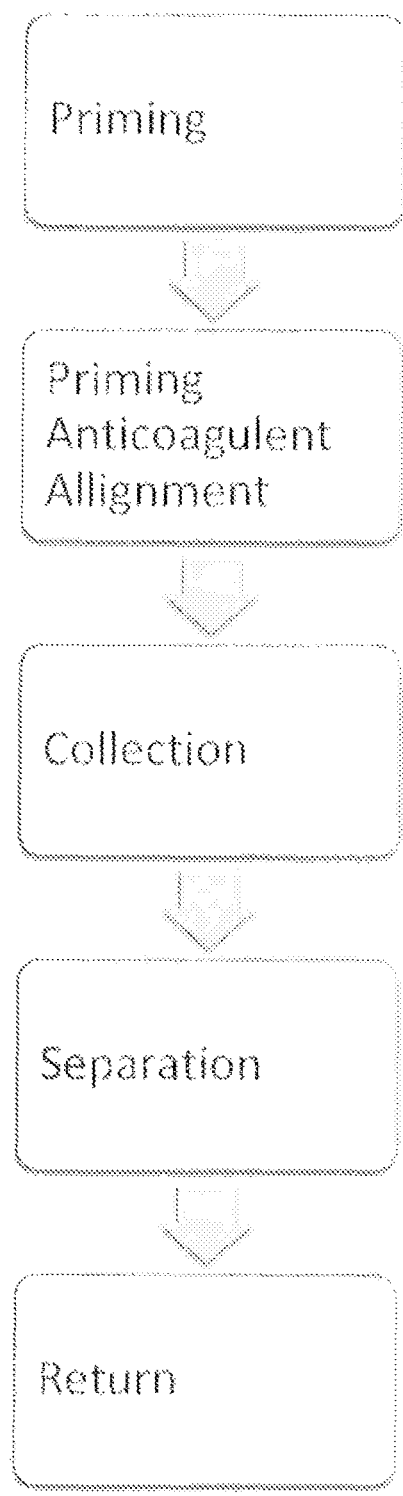

FIG. 3 is a flow chart of a blood collection process comprising the priming anticoagulant alignment method described herein. The process involves: Priming (synchronously advance pumps until anticoagulant is detected by withdraw/return liquid/air detector; Priming Anticoagulent Alignment (synchronously reverse pumps until anticoagulant is located at the priming anticoagulant alignment point); Collection (insert venous access device into donor's vein; advance pumps drawing whole blood from donor and mixing with anticoagulant); Separation (centrifugally separate blood components based on density; collect and retain desired component); and Return (return unneeded blood components to donor).

Figure 4:
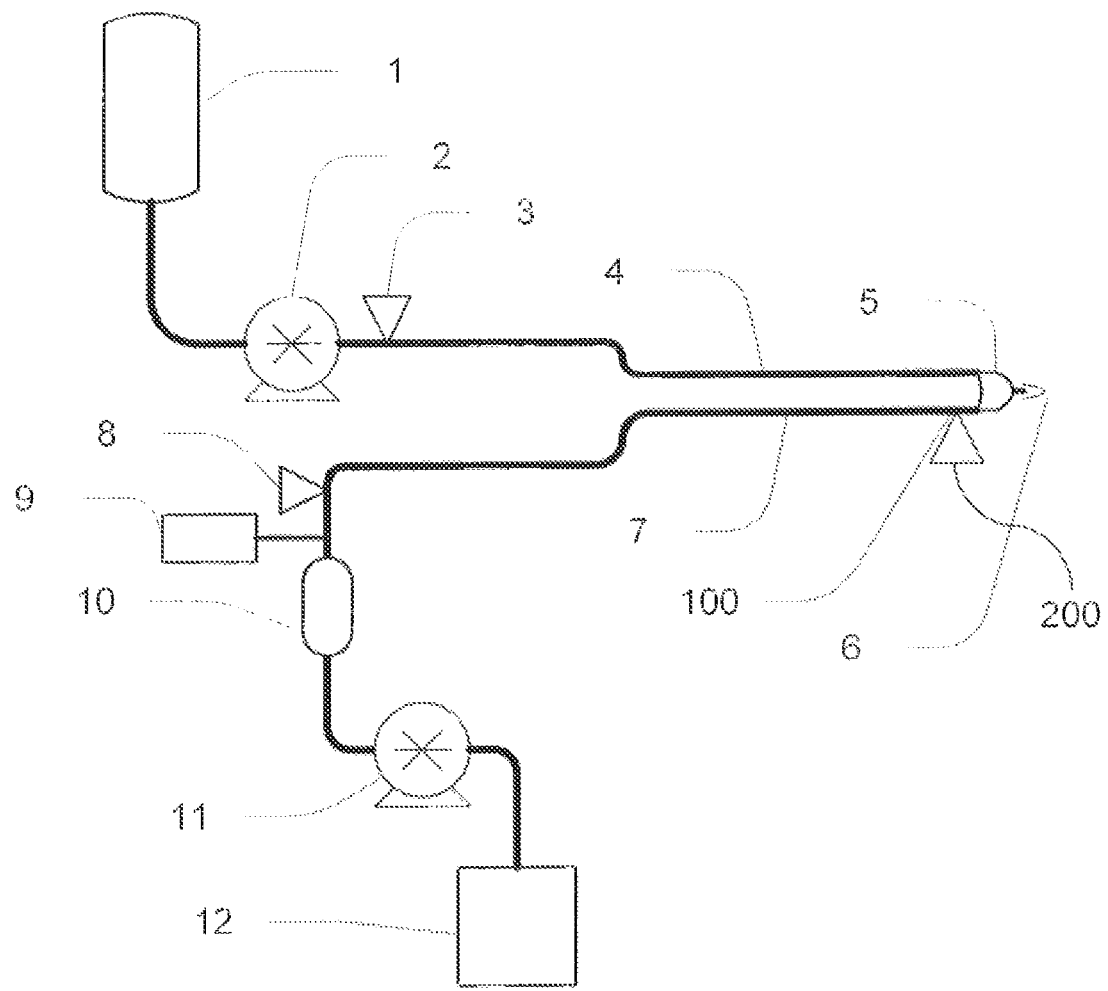

FIG. 4 is a schematic drawing of an exemplary blood collection system described herein that comprises a liquid/air detector 200 at the priming anticoagulant alignment point 100, adjacent to venous access device 5. The other components are the same as in FIG. 1.

FIG. 5 is a flow chart of a blood collection process comprising the priming anticoagulant procedure on a blood collection system that comprises at least one liquid/air detector 200 at the priming anticoagulant alignment point 100 adjacent to venous access device 5 as shown in FIG. 4. The process involves: Priming (synchronously advance pumps until anticoagulant is detected by withdraw/return liquid/air detector); Priming Anticoagulent Alignment (synchronously reverse pumps until anticoagulant is located at the priming anticoagulant alignment point; Collection (insert venous access device into donor's vein; advance pumps drawing whole blood from donor and mixing with anticoagulant); Separation (centrifugally separate blood components based on density; collect and retain desired component; and Return (return unneeded blood components to donor).

DETAILED DESCRIPTION

Blood is a tissue that transports oxygen and nutrients to the cells through the arteries and carries away carbon dioxide and waste products in the veins. Whole blood generally consists of cells suspended in a protein-rich fluid known as plasma. Three types of cells are found in blood: erythrocytes (red blood cells), leukocytes (white blood cells), and thrombocytes (platelets). Plasma is the liquid portion of blood and contains dissolved metabolites, electrolytes, and numerous proteins including albumin, clotting proteins, immunoglobulins. Whole blood can be separated into different components by various methods, including centrifugation, which employs differences in the densities of individual blood components. During centrifugation, the blood components establish themselves in layers according to their densities. Predetermined and well-known centrifuge speeds and time ratios are used to accomplish this separation. The erythrocytes (RBC), are the densest of the blood components, and consequently settle to the bottom of the fluid column. The leukocytes (WBC) which have intermediate density stratify as the "buffy coat" layer above the RBC layer. The least dense fraction of blood is the plasma that layers above the buffy coat. Platelets are suspended in the plasma and can be separated from plasma by additional centrifugation.

Whole blood will coagulate or "clot" shortly after removal from a donor unless an anticoagulant is added. Typical anticoagulants include calcium chelators such as ethylenediaminetetraacetic acid (EDTA), oxalate (oxalic acid) or citrate (citric acid). These anticoagulants function by chelating calcium ions in the blood that impedes clot formation (thrombosis). The most common anticoagulant is sodium citrate and/or citric acid suspended in a dextrose (glucose) solution.

Individual blood components can be collected from a donor by a process called apheresis, which employs equipment (collection equipment). Collection equipment may incorporate some disposable components in the fluid path to mitigate risks of transmission of infection among donors and to protect the purity of collected components. Anticoagulant may be introduced into the equipment prior to the collection as the disposable components are connected and equipment is made ready for collection. At the start of the collection process, a needle is inserted in the donor's arm that is connected to a separation device. Blood is gently drawn from the donor's vein, anticoagulant is added to the whole blood as it is drawn from the donor, and the anticoagulated blood mixture is pumped into the rotor of the cell separator where centrifugal force causes the components to separate. As the bowl fills and the additional fluid enters, die least dense components will exit first. The blood component that is to be collected is directed to a collection container or bag and the unwanted blood components are returned to the donor, sometimes after dilution. The process of drawing and returning continues until the quantity of the desired blood component has been collected, at which point the process is stopped and any uncollected blood components are returned.

Apheresis systems are used widely for the collection of single-donor platelets and single-donor plasma. A central feature of apheresis devices, however, is that, while they separate blood components at the point of collection, the unwanted blood components are returned to the donor. Accordingly, apheresis devices must incorporate a variety of safety features, such as air detectors and pressure monitors, to protect the donor from harm while blood components are collected and separated. Such safety mechanisms add complexity to apheresis system equipment but are essential for the safety and protection of the donor. Protections include measures to ensure that only desired components are returned to the donor (such as red blood cells), and potentially harmful substances such as pure anticoagulant or air are not introduced to the donor under any circumstances. Collection methods must also ensure that all blood drawn from a donor must be mixed with anticoagulant, to ensure that uncontrolled coagulation does not commence, possibly affecting the donor upon return of components, and possibly affecting the quality of the collected components.

A basic automated blood collection device used to carry out apheresis typically consist of: a reservoir holding anticoagulant solution; a pump far pumping the anticoagulant solution; a needle (or other cannula-like device) for insertion into a vein of the donor and drawing whole blood; a mixing means for mixing anticoagulant with whole blood (e.g., a Y-connector); a pump for pumping anticoagulated blood to the separator; a separator means; and reservoir for collecting the desired blood component; tubing for various inter-connections; valves for controlling the direction of flow and pressure; liquid/air sensors or detectors for determining the location of fluids within the tubes; and pressure sensors for determining the pressure of the fluid within the tubes or lines. As used herein the terms tube(s), tubing, and line(s) are used interchangeably to describe fluidic tubes through which liquid, such as blood, is capable of being pumped.

Specific examples of automated blood collection devices useful with the methods described herein are described in U.S. Pat. Nos. 5,387,187; 5,494,592; and 5,637,082 and WO 2009/129140 that are hereby folly incorporated by reference for their descriptions of such devices. Other useful collection devices would be recognized by one having ordinary skill in the art.

Described herein is a method for performing a blood collection procedure whereby the volume of anticoagulant utilized during the procedure is reduced thereby preventing dilution of the collected blood components and increasing the volume of components collected for a given overall volume. Specific aspects of the devices and methods described herein optimize the volume of whole blood withdrawn from a donor and the return of unharvested or processed blood components to the donor by reducing the anticoagulant used to prime the system. The device and method may use multiple liquid/air sensors on the withdraw and/or return tubing, in conjunction with pumps and control sequencing to determine the specific location of anticoagulant solution or whole blood and control the flow of fluids within the system based on the particular location within the system. Details of illustrative aspects are discussed below. The devices and methods described herein prevent any chance of air or undiluted anticoagulant from being accidently injected into a donor. This is accomplished by integrating a confirmation of proper fluidic control of the anticoagulant position and confirming that the donor has not been connected out of sequence (early).

Figure 1:
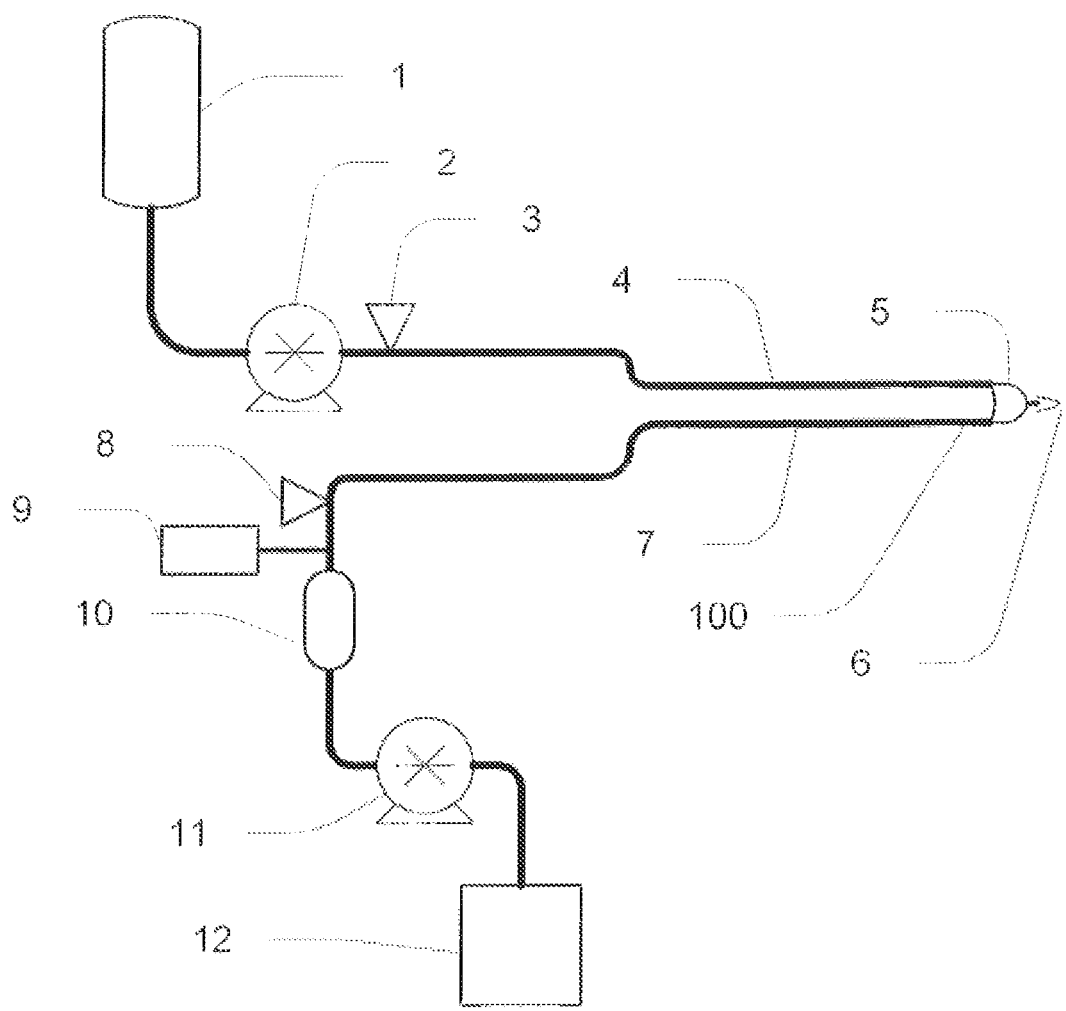
FIG. 1 is a schematic drawing of an exemplary blood collection system useful for carrying out the methods described herein (not to scale). Exemplary components of the blood collection system are as follows.

By way of introduction, a general, non-limiting, exemplary apheresis process is described to provide a basis for demonstrating a method described herein. FIG. 1 provides a schematic of a non-limiting, exemplary apheresis system (not to scale). FIG. 2 shows a flow chart of a general non-limiting, exemplary apheresis process.

An apheresis blood collection device is typically primed with anticoagulant prior to the collection of a donor's blood. This may be done to ensure the availability and fluidic control of anticoagulant for ratio based addition during the subsequent collection phase. During priming, anticoagulant contained in the anticoagulant reservoir 1 is pumped by means of an anticoagulant pump 2 via an anticoagulant tubing 4 through a capped Y-connector and venous access device 5 and through a withdraw/return line 7 by a withdraw/return pump 11 until liquid is detected by a liquid/air sensor 8. The pressure of the system is monitored by pressure sensor 9. Valves (not shown) may be used to control the direction of liquid flow and the pressure of the system. In a typical case, at the conclusion of anticoagulant priming, a continuous volume of anticoagulant is fluidly located from the anticoagulant reservoir 1 to the liquid/air sensor 8 in the withdraw/return tubing 7. Priming is complete when anticoagulant is detected by the liquid/air sensor 8.

After the priming step, the cap 6 of the Y-connector and venous access device 5 is removed and the venous access device 5 is connected to a vein of a donor and blood collection commences. The venous access device 5 can be connected to any number of devices capable of accessing a donor's veins including, but not limited to a phlebotomy needle (not shown). The Y-connector and venous access device 5 permits collected whole blood to mix with anticoagulant at the point of collection.

During the collection process, collected/anticoagulated blood is pumped by the withdraw/return pump 11 and flows from the venous access device 5 through the withdraw/return line 7, through an optional filter 10, to the separation and collection components 12 (not illustrated in detail). As the system draws the whole blood from the donor, the system may introduce anticoagulant into the withdrawn whole blood to prevent the blood from coagulating within the line 7, within the blood component separation device 12, or within the collected components after separation not shown). Anticoagulant can be dispensed into the system at a specific volumetric ratio of anticoagulant to anticoagulated blood (i.e., the mixture of anticoagulant and whole blood). The volume of anticoagulated blood collected by the collection system depends on the donor's weight (see Table 1). For plasma collection, the ratio of anticoagulant to anticoagulated blood may be 1:16 (i.e., 0.06; one part 4% sodium citrate anticoagulant for every 16 parts of anticoagulated blood). See FDA Volume Limits.

The anticoagulant pump 2, through which the anticoagulant tube 4 passes, controls the flow of anticoagulant within the anticoagulant line 4 and the anticoagulant introduced into the line is synchronous with the pumping of whole blood by pump 11. The volume of anticoagulant pumped is not identical to the volume of whole blood but rather the anticoagulant is introduced into the system at a specified ratio. See Table 1. Although the anticoagulant can be added to the whole blood at any point of the system, the anticoagulant is typically introduced as close as possible to the venous-access device 5 to permit the anticoagulant to mix with the whole blood and prevent coagulation of the blood upon removal from the donor. The anticoagulant line 4 may also include an optional bacteria filter (not shown) that prevents any bacteria in the anticoagulant reservoir 1, the anticoagulant, or the anticoagulant line 4 from entering the collection system and/or the donor. The collector may optionally have valves (not shown) that prevent backflow of a donor's blood into the anticoagulant lines. Additionally, the anticoagulant line 4 typically includes a liquid/air detector 3 that detects the presence of air within the anticoagulant line. The presence of air bubbles within any of the system lines can be problematic for the operation the system, indicate an absence of fluidic control that enables ratioed metering of anticoagulant to blood, and may even be harmful to the donor if the air bubbles enter the bloodstream. Therefore, at least one liquid/air detector 3 may be connected to an interlock (not shown) that stops the flow within the anticoagulant tube 4 in the event that air bubbles are detected (e.g., by stopping the anticoagulant pump 3 or closing a valve on the anticoagulant line 4), thereby preventing the air bubbles from entering a donor's bloodstream. The blood component separation device 12 separates the whole blood into several blood components. For example, the blood component separation device 12 may separate the whole blood into a first, second, third, and, perhaps, a fourth blood component. More specifically, the blood component separation device can separate the whole blood into plasma, red blood cells, white blood cells, and perhaps, platelets.

A non-limiting, exemplary blood component separation device 12 is a standard Latham-type centrifuge. The blood component separation device 12 separates she whole blood into its constituent components (e.g., red blood cells, white blood cell, plasma, and platelets). Although a Latham type centrifuge is mentioned above as a non-limiting example, other types of separation chambers and devices may be used, such as, without limitation, an integral blow-molded centrifuge bowl as described in U.S. Pat. Nos. 4,983,156 and 4,943, 273, which are hereby incorporated by reference for their description of such devices.

After the blood component separation device 12 separates and collects the desired component(s), the system can return the remaining components to the donor. The returned components may optionally be diluted with physiological saline or anticoagulant prior to returning to the donor. The system may use the withdraw/return pump 11 to return the components to the donor via the withdraw/return line 7, which fluidly connects the blood component separation device 12 and the venous-access device 5. Other aspects described herein may use a separate pump and/or return line (not shown). The withdraw/return line 4 may also include a filter 10 that prevents particulate or bacteria from (re)entering the system and/or the donor.

The blood component separation device may iteratively withdraw blood from the donor; separate the blood components; collect and save the desired component; and return the unneeded components to the donor in a cyclic manner until a determined quantity (weight) of the desired blood component is obtained. The blood component separation device may determine whether a specified amount of the desired blood component has been collected by measuring the mass or volume of the collected component. Accordingly, the blood component separation device can iteratively withdraw, separate, and return blood components until the specified quantity of the desired blood component has been obtained.

In the foregoing non-limiting example of a general blood collection device, the specific volume of priming anticoagulant fluidly located in the lines from the capped Y-connector and venous access device 5 to the liquid/air sensor 8 in the withdraw/return line 7 is not essential and comprises excess "priming anticoagulant" that upon separation by density will contribute surplus liquid volume to the collected components of similar density. Accordingly, this volume of priming anticoagulant will unnecessarily dilute the collected components by such volume. In blood collection devices that measure the obtained blood component by weight, this excess anticoagulant counts against the net weight of the collection and thus undercuts the quantity of blood component obtained from the donor. Further, the priming anticoagulant has a density similar to that of plasma. Thus, the anticoagulant fractionates in the separator 12 with the blood plasma, and thereby increases the volume and dilutes the concentration of collected plasma. Dilution of the collected plasma with this volume of priming anticoagulant can impair subsequent uses of the collected plasma, such as in downstream fractionation and subsequent manufacturing steps. The methods and devices described herein are useful for overcoming these potentially undesirable issues.

In one aspect described herein, a standard apheresis device is used and additional steps are added to the sequence of priming the system with anticoagulant. Compare FIGS. 2 and 3. As discussed above, the blood collection device is primed by pumping (e.g., pump 2) anticoagulant from the anticoagulant reservoir 1 through the liquid/air sensor 3 and anticoagulant line 4, to the capped Y-connector and venous access device 5 and continuing through the withdraw/return line 7 by the withdraw/return pump 11 until anticoagulant liquid is detected by the withdraw/return line liquid/air sensor 8. The pressure of the system is monitored by pressure sensor 9. At the conclusion of this step, a continuous volume of anticoagulant solution is fluidly connected from the anticoagulant reservoir 1 to the liquid/air sensor 8 in the withdraw/return line 7. In one aspect described herein, both pumps 2 and 11 are synchronously reversed for a determined number of revolutions, or for a determined time, or determined volume so as to reverse the anticoagulant/air interface boundary from the liquid/air sensor 8 immediately distal to the withdraw/return line 7 side of the capped Y-connector and venous access device 5 to the location marked 100, i.e., hereafter referred to as "the priming anticoagulant alignment point" 100.

Alternatively stated, the primed anticoagulant is pumped in reverse (counterclockwise direction, via pumps 2, and 11, respectively) through the system lines (e.g., the anticoagulant 4 and withdraw/return lines 7, respectively) so that a reduced volume of anticoagulant exists within the withdraw/return line 7 adjacent to the efferent side of the capped Y-connector and venous access device 5, with respect to the anticoagulant reservoir, i.e., at the priming anticoagulant alignment point 100. A reduced volume of anticoagulant comprises enough anticoagulant to adequately fill the Y-connector and venous access device 5 and a region of the priming anticoagulant alignment point 100, to prevent the anticoagulant-air interface from nearing the Y-connector and venous access device 5. The volume of anticoagulant that is present in a typical collection system in the lines between the Y-connector and fluid air sensor is approximately 12 mL in the lines on equipment. The lines are required to have adequate length to span between the fixed collection equipment and comfortably drape to either arm preferred by the donor. A portion of this volume of anticoagulant (i.e. ~11 mL) can be reduced by the flow reversal method described herein. The reduced volume of anticoagulant can comprise about 11.5 mL, or about 10.5 mL, or 10 mL, or about 9 mL, or about 8 mL, or about 7 ml, or about 6 mL, or about 5 mL, or about 4 mL, or about 3 mL, or about 2 mL, or about 1 mL, or about 0.5 mL, or about 0.2 mL, or about 0.1 mL of anticoagulant in the priming anticoagulant alignment point 100 depending on the geometry of the lines of the blood collection system.

At the conclusion of this reversal, anticoagulant remains in a continuous fluid path from the reservoir, through the pump 2, past the Y connector 5 to the priming anticoagulant alignment point 100. The system is then prepared with anticoagulant for collection: anticoagulant is under fluidic control of pump 2, and present at the point where blood will enter at the Y connector 5. Accordingly, the priming anticoagulant has been aligned within the blood collection device so as to reduce the volume of anticoagulant that exists within the collection lines prior to commencing blood collection. As used herein, "aligning the anticoagulant" within a blood collection device refers to any process or step that reduces the volume of anticoagulant within the lines of a blood collection device.

The methods for priming a blood collection device prior to blood collection described herein prevent excess anticoagulant in the withdraw/return line. Such aspects as described herein are referred to as "priming anticoagulant alignment."

One aspect described herein is directed to the sequence of events that prepares the blood collection equipment for collection. The anticoagulant priming commences with pump 2 and pump 11, synchronously pumping as anticoagulant is drawn from the anticoagulant reservoir 1. The device will record when liquid is detected at liquid/air sensor 3, and tally the number of pump revolutions required by pumps 2 and 11 to pump anticoagulant liquid from liquid/air sensor 3 through the anticoagulant and withdraw/return lines to reach liquid/air sensor 8. Once anticoagulant is detected at liquid/air sensor 8, both pump 2 and pump 11 stop.

Some other aspects described herein evaluate the measurement of volume/revolutions/time between liquid/air sensors as an additional check, on the proper function of the setup (tubing lengths, pump operation), and report any discrepancies to the operator and/or elect not to execute the reverse portion of the priming sequence. This tally, combined with expectations of the relative tubing geometry between air detectors at 3 and 8, can be used to infer the number of rotations to return the anticoagulant/air air interface boundary to the priming anticoagulant alignment point 100.

During the first part of the priming sequence, because the anticoagulant/air interface boundary is at a known location (such as air detector 8), the proper functioning of pumps 2 and 11 and the integrity of the cap 6 on the venous access device 5 can be verified by pausing one of either pump 2 or 11, and commencing pumping of other pump for a finite displacement. The proper seal and volumetric displacement of the pumps 2 and 11, in addition to the integrity of cap 6 will be evident by a change in monitored pressure at pressure sensor 9, because a finite volume of air (present between the anticoagulant air boundary and pump 11) is compressed in volume by pump displacement of a known volume. If proper function of the pumps or seal integrity is not confirmed at this step, the equipment may report an error for an operator to correct and/or elect not to execute the reverse portion of the priming sequence.

In order to remove excess anticoagulant from the withdraw/return line 7, both pumps 2 and 11 begin pumping in reverse (counterclockwise), so as to pump a quantity of anticoagulant present in withdraw/return line 7 through the Y-connector and venous access device 5, and into anticoagulant line 4. The reverse pumping ceases when anticoagulant reaches the priming anticoagulant alignment point 100, before the point where the boundary between air and anticoagulant reaches the venous access device 5. In other words, some anticoagulant remains in the priming anticoagulant alignment point 100 past the venous access device 5.

In some other aspects described herein, pumps 2 and 11 may reverse for a determined displacement volume. In other aspects described herein, pumps 2 and 11 may reverse for a determined number of revolutions that corresponds to a fixed displacement volume. In other aspects described herein, pumps 2 and 11 may reverse at a constant speed for a determined amount of time that corresponds to a fixed displacement volume. In other aspects described herein, pumps 2 and 11 may reverse while an operator observes the displacement and determines that the anticoagulant has readied the priming anticoagulant alignment point 100.

In other aspects described herein, the amount of reversal (either in time or rotations) may be calculated relative amount of time or rotations that had been required to initially progress the anticoagulant/air interface boundary between other air detection measurement points such as air detectors 3 and 8. In other aspects described herein, pumps 2 and 11 may reverse until the anticoagulant/air interface boundary reaches a physical sensor located along tubing at point 100 is reached.

In another aspect described herein, there is no pump reversal during the priming cycle. Pumps 2 and 11 operate synchronously for a certain period past the moment that AC passes air detector 3 and then stop as the anticoagulant/air boundary reaches the anticoagulant alignment point 100. The period of extra operation may be defined in terms of time, flow, or pump rotations.

In another aspect described herein, a blood collection device comprises a liquid/air detector 200 that is located in the blood collection system immediately adjacent to the Y-connector and venous access device 5 and adjacent to the draw/return line 7 (i.e., within the priming anticoagulant alignment point 100). See FIG. 4. Such a liquid/air detector permits 200 direct detection of the position of anticoagulant, air, or the anticoagulant/air interface at the priming anticoagulant alignment point 100. In such an aspect described herein, the priming alignment step is unnecessary because anticoagulant does not fill the withdraw/return line. Consequently, upon detection of anticoagulant at the liquid/air detector 200 positioned in the priming anticoagulant alignment point 100, blood collection and separation may commence upon insertion of a needle in a donor's arm and attaching the venous access device 5. See FIG. 5. In such an aspect described herein, the collection procedure is analogous to the ordinary operation of a standard blood collection process. Compare FIG. 2 with FIG. 5.

Some aspects described herein are shown in the following non-limiting examples.

EXAMPLES

Non-limiting examples described herein can be demonstrated using a PCS® 2 plasma collection systems fur die collection of platelet-poor plasma (Haemonetics, Braintree, Mass.). The amount of blood collected from a donor for use in apheresis is regulated by the U.S. Food and Drug Administration and prescribed in 21 C.F.R. §640.65. See Table 1. This regulation references a memorandum from Kathryn C. Zoon, Director, FDA Center for Biologies Evaluation and Research, Volume Limits for Automated Collection of Source Plasma (Nov. 4, 1992); and see Compliance Policy Guide §252.110 Volume Limits for Automated Collection of Source Plasma (Mar. 6, 2000). The amount of anticoagulant (a 4% sodium citrate solution) that is added to the whole blood is based on a ratio of anticoagulant to anticoagulated blood. The Center for Biologies Evaluation and Research (CBER) developed a nomogram that specifies the maximum volume of plasma that can be collected from a donor, based on the donor's weight.

The amount of plasma collected by the donor is not directly measured during the collection process; it is only measured in combination with anticoagulant. See Table 1. The collection devices are programmed to cease collection when a certain target collection volume is collected. The volume is based on a 1:16 (0.06) ratio of anticoagulant to anticoagulated-blood. See *FDA Volume Limits*. During collection, the volume collected is estimated based on the weight of the anticoagulated plasma (i.e., anticoagulant is added to whole blood that has been centrifugally fractionated into plasma).

TABLE 1

Volume Limits for Automated Collection of Source Plasma

| Donor Weight | Plasma Volume or Weight | Collection Volume or Weight |
|---|---|---|
| 110-149 lbs (50-68 kg) | 625 mL (640 g)* | 690 mL (705 g) |
| 150-174 lbs (68-79 kg) | 750 mL (770 g) | 825 mL (845 g) |
| 175 lbs and up (>80 kg) | 800 mL (820 g) | 880 mL (900 g) |

See Kathryn C. Zoon, Director, FDA Center for Biologies Evaluation and Research, Volume Limits for Automated Collection of Source Plasma, (Nov. 4, 1992) and Compliance Policy Guide § 252.110 Volume Limits for Automated Collection of Source Plasma (Mar. 6, 2000).

TABLE 1-continued

Volume Limits for Automated Collection of Source Plasma

| Donor Weight | Plasma Volume or Weight | Collection Volume or Weight |
|---|---|---|

*Assuming a density of approximately 1.026 g/mL for human plasma.

lected plasma of up to 1.2-1.7%, and reduces the overall protein concentration by up to 1.2-1.7%, depending on the weight of the donor and efficiency of the separator. See Table 2.

TABLE 2

Calculated Potential Lost Plasma Volumes and Concentration Reductions Due to Priming Anticoagulant

| Donor Weight | Plasma Volume or Weight | Collection Volume or Weight | Lost Plasma Volume | Reduced Plasma Concentration |
|---|---|---|---|---|
| 110-149 lbs (50-68 kg) | 625 mL (640 g) | 690 mL (705 g) | 1.7% | 1.7% |
| 150-174 lbs (68-79 kg) | 750 mL (770 g) | 825 mL (845 g) | 1.4% | 1.4% |
| 175 lbs and up (>80 kg) | 800 mL (820 g) | 880 mL (900 g) | 1.3% | 1.3% |

FIG. 1 depicts a general set up of a PCS® 2 plasma collection system. The current process of the PCS® 2 plasma collection system begins with anticoagulant priming. During this step anticoagulant (4% sodium citrate) is pumped from its reservoir 1 (a sterile IV-bag) by the anticoagulant pump 2 through the anticoagulant line 4 and capped Y-connector and venous access device 5, continuing through the withdraw/return line 7 until the anticoagulant liquid is detected by the liquid/air detector 8. During this priming step, both pumps 2 and 11 turn at the same rate (i.e., same volume displacement) until anticoagulant is detected by the liquid/air detector 8. In the PCS® 2 plasma collection system, approximately 11.4 mL of 100% anticoagulant exists between the Y-connector and venous access device 5 and the liquid/air detector 8. The donor is then connected by removing the cap 6 from the Y-connector and venous access device 5 and inserting the venous access device 5 into a vein of the donor's arm.

When the donation cycle commences, the volume of 100% anticoagulant contained in the withdraw/return line between the Y-connector and venous access device 5 and the liquid/air detector 8 (approximately 11.4 mL) is pumped into the separator preceding the flow of anticoagulated blood (the mixture of whole blood and anticoagulant mixed at the Y-connector and venous access device 5). During blood collection, the anticoagulant pump 2 pumps at a rate $\frac{1}{16}$ of the rate of the withdraw/return pump 11. This rate differential produces a 1:16 ratio of anticoagulant to anticoagulated blood as prescribed by the FDA Volume Limits. After separation, the anticoagulated plasma is collected and the erythrocytes, leukocytes, and platelets are returned to the donor through the withdraw/return line 7.

During separation via centrifugation, the anticoagulant, which has a density similar to water (ca. 1.022 g/mL), separates with the blood plasma (ca. 1.026 g/mL). Consequently, the approximately 11.4 mL (~11.4 g) of 100% anticoagulant from priming increases the volume of the plasma component in the resultant collection by up to 1.7%. Furthermore, the plasma collection endpoint is determined by the weight of anticoagulated plasma collected. The 11.4 mL of 100% anticoagulant that is used to prime the system collection contributes to the endpoint weight and causes the blood collection cycle to stop prematurely (i.e., prior to reaching the collection volume or weight). This can result in a lost volume of col- While such losses and concentration reductions are relatively insignificant on a single donor basis, they compound on an industrial, production-scale, particularly in view of associated assaying and overhead costs. Consequently, the priming anticoagulant significantly reduces plasma yields and affects production efficiency.

Priming anticoagulant alignment eliminates the excess anticoagulant in the withdraw/return lines and prevents the associated volume losses and dilution effects. The method can be practiced without any modification to the plasma collection systems with the addition of one step to the collection process. This step can be implemented with appropriate interlocks to prevent any potential risk to the donor or quality of the collected components.

By way of a non-limiting example, the PCS® 2 system is primed as described above by pumping anticoagulant through the system past liquid/air detector 3, continuing until the anticoagulant liquid is detected by the liquid/air detector 8. The system setup can be checked for pressure integrity by noting absolute pressure at a sensor such as 9 and/or rotating one pump differently than another (such as one fixed, and the other moving slightly). As either pump propels either into or out a known volume of fluid and/or air, the change in pressure in that segment of the system can be measured by a pressure sensor such as 9. Attributes such as the relationship of pressure changes to volume changes can be compared to a range of system expectations previously established to represent appropriate setup and operation, and exclude inappropriate operation. Pressure integrity problems may indicate issues such as a failure to engage tubing properly in either pump, or the premature connection of the donor. Proper fluidic control of the system can be verified by comparing the observed characteristics of the fluid advancement between two liquid/air detectors (such as 3 and 8) for attributes such as time, rotations, or pump volume to a range of system expectations previously established to represent appropriate setup and operation.

Based on appropriate degree of confirmation that a proper setup is in place, both pumps 2 and 11 are synchronously reversed at the same rate either for a specified period of time, for a specified number of revolutions, or to pump a specified volume, or for an proportion or offset from the pump action required to advance the fluid between liquid/air sensors such as 3 and 8. This step results pumps the excess anticoagulant back through the system lines until the air/anticoagulant boundary becomes positioned within the priming anticoagulant alignment point 100. This step can be performed manually by an operator who observes or manually commands the revere pumping of the anticoagulant into the priming anticoagulant alignment point 100, however, an automated interlocked system is preferable to reduce any human variability in execution or detection of problems that might have any potential to adversely affect donor safety or the quality of the collected components. It is important that a volume of anticoagulant exists on the withdraw/return line side of the Y-connector and venous access device 5 in order to ensure that anticoagulant is present to be mixed with blood as it is collected. Targeting a small amount of anticoagulant (examples may include between about 0.5 and 10 mL) to be present between the priming anticoagulant alignment point 100 and the venous access device 5 is sufficient to reliably ensure that anticoagulant is present at the venous access device. This target volume range accounts for variability in collection tubing geometries and fluid control. This small amount of anticoagulant does not adversely affect plasma volume, concentration, or downstream processing, and is less than would be present if no pump reversal had occurred. After the priming anticoagulant alignment step, the typical operation of the PCS® 2 plasma collection system can continue as described above, beginning with inserting the venous access device into the donor's vein. Compare FIGS. 2 and 3.

When establishing the expectation ranges to be used for verification of the setup that enables reverse pumping during priming, consideration should be given to cost (such as risk of false alarms and cycle interruptions) versus risk (such as executing a the reverse pumping step when proper fluid control and the absence of the donor have not bee confirmed). The detection of equipment problems should cause an immediate notification and arrest the collection process. However, there may be operating regions where the only aspect of the cycle that may be questionable is the reverse pumping of the priming sequence. If the "cost" is limited to merely informing the operator that the reverse pumping would not be engaged on that donation (as opposed to prohibiting the donation from executing), this would allow tight expectation ranges to be established, with a benefit of confidence that any anomalous conditions will be reliably detected.

By way of another non-limiting example, the PCS® 2 system is primed as described above by pumping anticoagulant through the system until the anticoagulant liquid is detected by the liquid/air detector 3. At this point, both pumps 2 and 11 are synchronously advanced at the same rate either for a specified period of time, for a specified number of revolutions, or to pump a specified volume. This step results pumps the anticoagulant through the lines until the air/anticoagulant boundary becomes positioned within the priming anticoagulant alignment point 100. This approach would not have a means to automatically detect whether fluid control was compromised by potential events such as a failure to accurately engage tubing in pumps or a variation in the interior diameter of the tubing. This step can also be performed or verified manually by an operator who observes the pumping of the anticoagulant into the priming anticoagulant alignment point 100. It is important that an amount of anticoagulant exists on the withdraw/return line side of the Y-connector and venous access device 5 to ensure anticoagulant is present as blood is introduced upon connection. Targeting a small amount of anticoagulant (examples may include between about 0.5 and 10 mL) to be present between the priming anticoagulant alignment point 100 and the venous access device 5 is sufficient to reliably ensure anticoagulant is present at the venous access device given expectations for small variability in collection tubing geometries and fluid control on any specific donation. This small amount does not adversely affect plasma volume, concentration, or downstream processing. After the priming anticoagulant alignment step, the typical operation of the PCS® 2 plasma collection system can continue as described above, beginning with inserting the venous access device into the donor's vein.

The foregoing description has been presented only for the purpose of illustration and the description and is not intended to be exhaustive or to limit the embodiments or aspects described herein to the precise forms disclosed. Numerous modifications and adaptations thereof will be apparent to those having skill in the art without departing from the spirit and scope of the methods and devices described herein.

The scope of protection of the devices and methods described herein includes all combinations of embodiments, aspects, examples, steps, and preferences herein described.

What is claimed is:

1. A method of reducing anticoagulant dilution of collected blood components in a blood processing equipment, wherein the blood processing equipment comprises an anticoagulant reservoir (1) having an anticoagulant solution, a Y-connector and venous access device (5) having a cap (6), a blood component separation device (12), a line of anticoagulant (4) fluidly connecting the anticoagulant reservoir (1) to the Y-connector and venous access device (5), a blood withdraw/return line (7) fluidly connecting the Y-connector and venous access device (5) to the blood component separation device (12), an anticoagulant pump (2) fluidly connected to the line of anticoagulant (4), a liquid/air detector (3) fluidly connected to the line of anticoagulant (4), a withdraw/return pump (11) fluidly connected to the blood withdraw/return line (7), a pressure senor (9) fluidly connected to the blood withdraw/return line (7), and a liquid/air detector (8) fluidly connected to the blood withdraw/return line (7), the method comprising:
    (a) priming and aligning the blood processing equipment with the anticoagulant solution comprising:
        (i) synchronously pumping with pumps (2, 11) to advance the anticoagulant solution from the anticoagulant reservoir (1) until the anticoagulant is detected by the air/fluid sensor (8); and
        (ii) synchronously reverse pumping with pumps (2, 11) to clear the line of anticoagulant (4) until an air/anticoagulant interface boundary is present in a priming anticoagulant alignment point (100);
    (b) connecting the venous-access device (5) to a donor;
    (c) withdrawing whole blood from the donor such that the withdrawn whole blood is collected in the blood component separation device (12) for processing;
    (d) separating the withdrawn whole blood into a first blood component and a second blood component in the blood component separation device (12);
    (e) extracting the first blood component from the blood component separation device (12); and
    (f) returning the second blood component to the donor through the draw/return line (7).

2. The method of claim 1, further comprising the following steps between step (i) and step (ii):
    (1) confirming pump operation and tubing geometry by comparing the number of pump revolutions required to progress the anticoagulant between the liquid/air sensors (3, 8) to pre-established expectations derived from understanding of pump displacement and tubing length; and (2) confirming proper function of the pumps (2, 11) and the cap (6) on the venous access device (5) by holding one pump fixed, and moving the other, while comparing the observed pressure change at the pressure sensor (9), to an expected change given the volume of fluid vs air expected in the lines; and (3) annunciating any discrepancies to operator such that they can take appropriate action.

3. The method of claim 1, wherein the blood processing equipment further comprises a first liquid/air detector and a second liquid/air detector, wherein the first fluid/air detector is fluidly connected to the withdraw/return line (7) and immediately adjacent to the venous-access device (5), and wherein the second liquid/air detector is fluidly connected to the withdraw/return line (7) and between the first liquid/air detector and the withdraw/return pump (11).

4. The method of claim 1, wherein the first component comprises erythrocytes, leukocytes, platelets, or a combination thereof.

5. The method of claim 1, wherein the second component comprises plasma.

* * * * *